(12) United States Patent
Dubois et al.

(10) Patent No.: US 7,868,024 B2
(45) Date of Patent: Jan. 11, 2011

(54) DERIVATIVES OF N-(HETEROARYL)-1-HETEROARYL-1H-INDOLE-2-CARBOXAMIDES, PREPARATION THEREOF AND THERAPEUTIC USE THEREOF

(75) Inventors: Laurent Dubois, Paris (FR); Yannick Evanno, Paris (FR); André Malanda, Paris (FR); Christian Maloizel, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/504,869

(22) Filed: Jul. 17, 2009

(65) Prior Publication Data

US 2009/0306143 A1    Dec. 10, 2009

Related U.S. Application Data

(63) Continuation of application No. PCT/FR2008/000055, filed on Jan. 17, 2008.

(30) Foreign Application Priority Data

Jan. 19, 2007    (FR) .................................. 07 00357

(51) Int. Cl.
A61K 31/44    (2006.01)
C07D 401/06    (2006.01)

(52) U.S. Cl. .................. 514/339; 546/268.1; 546/268.4; 546/272.7; 546/273.4; 514/336; 514/337

(58) Field of Classification Search ............. 546/268.1, 546/268.4, 272.7, 273.4; 514/336, 337, 339
See application file for complete search history.

(56) References Cited

U.S. PATENT DOCUMENTS

| 7,384,969 B2 * | 6/2008 | Dubois et al. ............... 514/414 |
| 7,407,950 B2 * | 8/2008 | Dubois et al. ............ 514/211.09 |
| 7,557,134 B2 * | 7/2009 | Dubois et al. ............... 514/414 |
| 7,745,467 B2 * | 6/2010 | Dubois et al. ............... 514/339 |
| 2005/0165049 A1 | 7/2005 | Hulme et al. |

FOREIGN PATENT DOCUMENTS

| FR | 2874015 | 2/2006 |
| WO | WO 02/059110 | 8/2002 |
| WO | WO 03/049702 | 6/2003 |
| WO | WO 03/068749 | 8/2003 |
| WO | WO 2004/072069 | 8/2004 |
| WO | WO 2006/072736 | 7/2006 |
| WO | WO 2007010144 | 1/2007 |

OTHER PUBLICATIONS

Antilla, J. C., et al., Copper-Diamine-Catalyzed N-Arylation of Pyrroles, Pyrazoles, Indazoles, Imidazoles, and Triazoles, J. Org. Chem., (2004), vol. 69, pp. 5578-5587.
Williams, T. M., et. al, 5-Chloro-3-(Phenylsulfonyl)Indole-2-Carboxamide: A Novel, Non-Nucleoside Inhibitor of HIV-1 Reverse Transcriptase, J. Med. Chem., (1993), vol. 36: pp. 1291-1294.

* cited by examiner

*Primary Examiner*—Golam M Shameem
(74) *Attorney, Agent, or Firm*—Kelly Bender, Esq.; Scully, Scott, Murphy & Presser, P.C.

(57) ABSTRACT

The invention relates to compounds of formula (I):

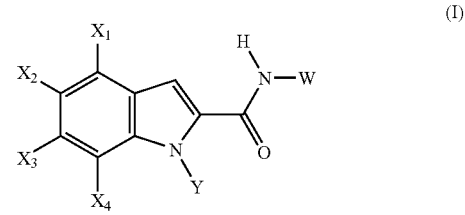

Wherein $X_1$, $X_2$, $X_3$, $X_4$, Y and W are as described herein. The invention also relates to a preparation method and to a therapeutic application.

20 Claims, No Drawings

DERIVATIVES OF N-(HETEROARYL)-1-HETEROARYL-1H-INDOLE-2-CARBOXAMIDES, PREPARATION THEREOF AND THERAPEUTIC USE THEREOF

CROSS REFERENCE TO RELATED APPLICATIONS

This application is a continuation of International application No. PCT/FR2008/000,055, filed Jan. 17, 2008, which is incorporated herein by reference in its entirety; which claims the benefit of priority of French patent application Ser. No. 07/00,357, filed Jan. 19, 2007.

BACKGROUND OF THE INVENTION

Field of the Invention

A subject-matter of the invention is compounds derived from N-(heteroaryl)-1-heteroaryl-1H-indole-2-carboxamides which exhibit an in vitro and in vivo antagonist activity for receptors of TRPV1 (or VR1) type.

A first subject-matter of the invention relates to the compounds corresponding to the general formula (I) below.

Another subject-matter of the invention relates to processes for the preparation of the compounds of the general formula (I).

Another subject-matter of the invention relates to the use of the compounds of the general formula (I) in particular in medicaments or in pharmaceutical compositions.

SUMMARY OF THE INVENTION

The compounds of the invention correspond to the general formula (I):

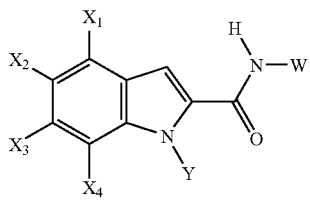

in which:

$X_1$, $X_2$, $X_3$, $X_4$ represent, independently of one another, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$ or aryl group, the aryl optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

W represents a fused bicyclic group of formula:

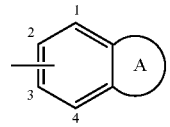

bonded to the nitrogen atom via the 1, 2, 3 or 4 positions;

A represents a 5- to 7-membered heterocycle comprising from one to three heteroatoms chosen from O, S or N;

the carbon atom or atoms of A optionally being substituted by one or more groups chosen from a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_3$-alkyleneoxy, aryl, aryl-$C_1$-$C_6$-alkylene, oxo or thio group;

the nitrogen atom or atoms of A optionally being substituted by $R_6$ when the nitrogen is adjacent to a carbon atom substituted by an oxo group, or by $R_7$ in the other cases;

Y represents a heteroaryl optionally substituted by one or more groups chosen from a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxyl, $C_1$-$C_6$-fluoroalkoxyl, $C_1$-$C_6$-thiofluoroalkyl, cyano, C(O)$NR_1R_2$, nitro, $NR_1R_2$, $C_1$-$C_6$-thioalkyl, SH, —S(O)—$C_1$-$C_6$-alkyl, —S(O)$_2$—$C_1$-$C_6$-alkyl, —S(O)—$C_3$-$C_7$-cycloalkyl, —S(O)$_2$—, $C_3$-$C_7$-cycloalkyl, $SO_2NR_1R_2$, $NR_3COR_4$, $NR_3SO_2R_5$, aryl-$C_1$-$C_6$-alkylene or aryl group, the aryl and aryl-$C_1$-$C_6$-alkylene optionally being substituted by one or more substitutes chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, a halogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ form, together with the nitrogen atom which carries them, an azetidinyl, pyrrolidinyl, piperidinyl, azepinyl, morpholinyl, thiomorpholinyl, piperazinyl or homopiperazinyl or group, this group optionally being substituted by a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of one another, a hydrogen atom or a $C_1$-$C_6$-alkyl, aryl-$C_1$-$C_6$-alkylene or aryl group;

$R_5$ represents a $C_1$-$C_6$-alkyl, aryl-$C_1$-$C_6$-alkylene or aryl group;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$—, aryl-$C_1$-$C_6$-alkylene-S(O)$_2$— or aryl group.

In the compounds of general formula (I):
the sulfur atom or atoms of the heterocycle A or of the heteroaryl Y can be in the oxidized form (S(O) or S(O)$_2$);
the nitrogen atom or atoms of the heterocycle A or of the heteroaryl Y can be in the oxidized form (N-oxide).

DETAILED DESCRIPTION OF THE INVENTION

In the context of the invention, mention may be made, as examples of group W, of the indolyl, isoindolyl, indolinyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolinyl, dihydroquinolinyl, tetrahydroquinolinyl, isoquinolinyl, dihydroisoquinolinyl, tetrahydroisoquinolinyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[1,4-b]diazepinyl, tetrahydrobenzo[1,4-e]diazepinyl, tetrahydrobenzo[1,4-b]oxazepinyl or tetrahydrobenzo[1,4-b]thiazepinyl groups.

Among the compounds of general formula (I) which are subject-matters of the invention, a first subgroup of compounds is composed of the compounds for which:

$X_1$, $X_2$, $X_3$ and $X_4$ represent, independently of one another, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)NR$_1$, R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$ or NR$_3$SO$_2$R$_5$ group.

Among the compounds of general formula (I) which are subject-matters of the invention, a second subgroup of compounds is composed of the compounds for which:

$X_1$, $X_2$, $X_3$ and $X_4$ represent, independently of one another, a hydrogen or halogen atom or a $C_1$-$C_6$-alkyl or $C_1$-$C_6$-fluoroalkyl group.

Among the compounds of general formula (I) which are subject-matters of the invention, a third subgroup of compounds is composed of the compounds for which:

$X_1$, $X_3$ and $X_4$ represent a hydrogen atom.

Among the compounds of general formula (I) which are subject-matters of the invention, a fourth subgroup of compounds is composed of the compounds for which:

$X_1$, $X_3$ and $X_4$ represent a hydrogen atom and $X_2$ represents a halogen atom, more particularly a fluorine atom.

Among the compounds of general formula (I) which are subject-matters of the invention, a fifth subgroup of compounds is composed of the compounds for which:

W represents a fused bicyclic group of formula:

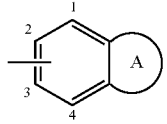

bonded to the nitrogen atom via the 1, 2, 3 or 4 positions;

and W is chosen from the indolyl, isoindolyl, indolinyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolinyl, dihydroquinolinyl, tetrahydroquinolinyl, isoquinolinyl, dihydroisoquinolinyl, tetrahydroisoquinolinyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[1,4-b]diazepinyl, tetrahydrobenzo[1,4-e]diazepinyl, tetrahydrobenzo[1,4-b]oxazepinyl, tetrahydrobenzo[1,4-b]thiazepinyl groups;

the carbon and/or nitrogen atom or atoms of the said group W optionally being substituted as defined in the general formula (I).

Among the compounds of the general formula (I) which are subject-matters of the invention, a sixth subgroup of compounds is composed of the compounds for which:

W represents an indolyl group; the carbon atom and/or nitrogen atom or atoms of the said group W optionally being substituted as defined in the general formula (I).

Among the compounds of general formula (I) which are subject-matters of the invention, a seventh subgroup of compounds is composed of the compounds for which:

W is chosen from the benzimidazolyl and indolyl groups; and/or the carbon atom or atoms of A optionally being substituted by one or more $C_1$-$C_6$-alkyl groups, or particularly methyl groups; and/or the nitrogen atom or atoms of A optionally being substituted by R$_7$, R$_7$ representing a $C_1$-$C_6$-alkyl group, or particularly a methyl group.

Among the compounds of general formula (I) which are subject-matters of the invention, an eighth subgroup of compounds is composed of the compounds for which:

W is chosen from the benzimidazol-5-yl and indol-5-yl group; and/or the carbon atom or atoms of A optionally being substituted by one or more $C_1$-$C_6$-alkyl groups, more particularly a methyl; and/or the nitrogen atom or atoms of A optionally being substituted by R$_7$, R$_7$ representing a $C_1$-$C_6$-alkyl group, more particularly a methyl.

Among the compounds of general formula (I) which are subject-matters of the invention, a ninth subgroup of compounds is composed of the compounds for which:

Y represents a pyridinyl optionally substituted by one or more $C_1$-$C_6$-alkyl groups, more particularly a methyl.

The compounds for which $X_1$, $X_2$, $X_3$, $X_4$, W and Y are simultaneously as defined in the above subgroups of compounds form a tenth subgroup.

In the context of the present invention:
$C_t$-$C_z$, where t and z can take the values from 1 to 7, is understood to mean a carbon chain which can have from t to z carbon atoms, for example $C_1$-$C_3$ is understood to mean a carbon chain which can have from 1 to 3 carbon atoms;
an alkyl is understood to mean a saturated, linear or branched, aliphatic group. Mention may be made, by way of examples, of the methyl, ethyl, propyl, isopropyl, butyl, isobutyl, tert-butyl or pentyl groups, and the like;

an alkylene is understood to mean a saturated, linear or branched, divalent alkyl group; for example, a $C_{1-3}$-alkylene group represents a divalent carbon chain of 1 to 3 carbon atoms which is linear or branched, more particularly a methylene, ethylene, 1-methylethylene or propylene;

an alkyleneoxy is understood to mean an alkylene comprising an oxygen atom;

a cycloalkyl is understood to mean a cyclic carbon group. Mention may be made, by way of examples, of the cyclopropyl, cyclobutyl, cyclopentyl or cyclohexyl groups, and the like;

a fluoroalkyl is understood to mean an alkyl group, one or more hydrogen atoms of which have been substituted by a fluorine atom;

an alkoxyl is understood to mean an —O-alkyl radical where the alkyl group is as defined above;

a cycloalkoxyl is understood to mean an —O-cycloalkyl radical where the cycloalkyl group is as defined above;

a fluoroalkoxyl is understood to mean an alkoxyl group, one or more hydrogen atoms of which have been substituted by a fluorine atom.

a thioalkyl is understood to mean an —S-alkyl radical where an alkyl group is as defined above;

a thiofluoroalkyl is understood to mean a thioalkyl group, one or more hydrogen atoms of which have been substituted by a fluorine atom;

an aryl is understood to mean an aromatic cyclic group comprising between 6 and 10 carbon atoms. Mention may be made, as examples of aryl groups, of the phenyl or naphthyl groups;

a heterocycle is understood to mean an aromatic, partially unsaturated or saturated 5- to 12-membered group comprising from one to five heteroatoms chosen from O, S or N;

mention may be made, as examples of heterocycle, of the azetidinyl, pyrrolidinyl, piperidinyl, azepinyl, morpholinyl, thiomorpholinyl, piperazinyl, homopiperazinyl, dihydrooxazolyl, dihydrothiazolyl, dihydroimidazolyl, dihydropyrrolyl, tetrahydropyridinyl, imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl or triazinyl groups;

a heteroaryl is understood to mean an aromatic, 5- to 14-membered, mono-, bi- or tricyclic heterocyclic group comprising from 1 to 8 heteroatoms chosen from O, S or N;

mention may be made, as examples of monocyclic heteroaryl, of the imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl or triazinyl groups;

mention may be made, as examples of bicyclic heteroaryl, of the indolyl, isoindolyl, benzofuranyl, benzothiophenyl, benzoxazolyl, benzimidazolyl, indazolyl, benzothiazolyl, isobenzofuranyl, isobenzothiazolyl, isoquinolinyl, pyrrolo[2,3-c]pyridinyl, pyrrolo[2,3-b]pyridinyl, pyrrolo[3,2-b]pyridinyl, pyrrolo[3,2-c]pyridinyl, quinolinyl, isoquinolinyl, cinnolinyl, quinazolinyl or quinoxalinyl groups;

mention may be made, as examples of tricyclic heteroaryl, of the pyrido[1,2-a]benzimidazolyl, thiazolo[1,2-a]benzimidazolyl or imidazo[1,2-a]benzimidazolyl groups;

a halogen atom is understood to mean a fluorine, a chlorine, a bromine or an iodine;

"oxo" is understood to mean "=O";

"thio" is understood to mean "=S".

The compounds of formula (I) can comprise one or more asymmetric carbon atoms. They can exist in the form an enantiomers or diastereoisomers. These enantiomers or diastereoisomers, and also their mixtures, including racemic mixtures, form part of the invention.

The compounds of formula (I) can exist in the form of bases or of addition salts with acids. Such addition salts form part of the invention.

These salts are advantageously prepared with pharmaceutically acceptable acids but the salts of other acids of use, for example, in the purification or isolation of the compounds of formula (I) also form part of the invention.

The compounds of the general formula (I) can occur in a form of hydrates or of solvates, namely in the form of combinations or of associations with one or more molecules of water or with a solvent. Such hydrates and solvates also form part of the invention.

In that which follows, the term "leaving group" is understood to mean a group which can easily split from a molecule by cleaving a heterolytic bond, with departure of an electron pair. This group can thus be easily replaced by another group during a substitution reaction, for example. Such leaving groups are, for example, halides or an activated hydroxyl group, such as a methanesulfonate, benzenesulfonate, p-toluenesulfonate, triflate, acetate, and the like. Examples of leaving groups and also of the references for their preparation are given in "Advances in Organic Chemistry", J. March, 5$^{th}$ Edition, Wiley Interscience, 2001.

In accordance with the invention, the compounds of general formula (I) can be prepared according to the process illustrated by the following Scheme 1.

According to Scheme 1, the compounds of general formula (IV) can be obtained by reaction of a compound of general formula (II), in which $X_1$, $X_2$, $X_3$ and $X_4$ are as defined in the general formula (I) and D represents a $C_1$-$C_6$-alkoxyl group, with a compound of general formula (III), in which Y is as defined in the general formula (I) and LG represents a leaving group or LG represents a hydroxyl group.

The reaction can be carried out in the presence of a base, such as potassium carbonate or tripotassium phosphate preferably in the presence of a catalytic amount of a metal salt, such as copper iodide, and of an additive, such as 1,2-dimethylaminocyclohexane (Buchwald S. L., *J. Org. Chem.*, 2004, 69, 5578-5587).

The compound of general formula (I) is subsequently obtained by reaction of a compound of general formula (IV), as obtained above, with an amide of the compound of general formula (V), in which W is as defined in the general formula (I), at reflux of a solvent, such as toluene. The amide of the compound of general formula (V) is prepared by prior action of trimethylaluminum on the amines of general formula (V).

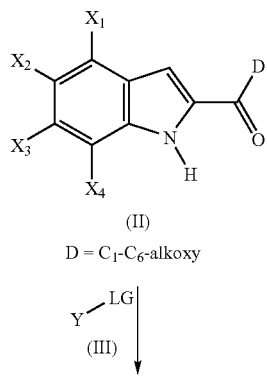

Scheme 1

(II)

D = $C_1$-$C_6$-alkoxy (III)

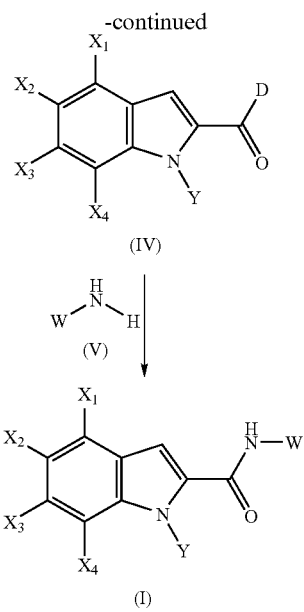

The compounds of general formulae (I), (II) and (IV) in which $X_1$, $X_2$, $X_3$ and/or $X_4$ represent a cyano group or an aryl can be obtained by a coupling reaction catalyzed by a metal, such as palladium, carried out on the corresponding compounds of the general formulae (I), (II) and (IV) in which $X_1$, $X_2$, $X_3$ and/or $X_4$ represent a leaving group, for example a bromine, according to methods which are described in the literature or which are known to a person skilled in the art.

The compounds of general formulae (I), (II) and (IV), in which $X_1$, $X_2$, $X_3$ and/or $X_4$ represent a $C(O)NR_1R_2$ group can be obtained from the corresponding compounds of general formulae (I), (II) and (IV) in which $X_1$, $X_2$, $X_3$ and/or $X_4$ represent a cyano group according to methods which are described in the literature or which are known to a person skilled in the art.

The compounds of general formulae (I), (II) and (IV) in which $X_1$, $X_2$, $X_3$ and/or $X_4$ represent an —S(O)—$C_1$-$C_6$-alkyl or —S(O)$_2$—$C_1$-$C_6$-alkyl group can be obtained by oxidation of the corresponding compounds of general formulae (I), (II) and (IV) in which $X_1$, $X_2$, $X_3$ and/or $X_4$ represent a $C_1$-$C_6$-thioalkyl group according to methods which are described in the literature or which are known to a person skilled in the art. The compounds of general formulae (I), (II) and (IV) in which $X_1$, $X_2$, $X_3$ and/or $X_4$ represent an $NR_1R_2$, $NR_3COR_4$ or $NR_3SO_2R_5$ group can be obtained from the corresponding compounds of general formulae (I), (II) and (IV) in which $X_1$, $X_2$, $X_3$, and/or $X_4$ represent a nitro group, for example by reduction and then acylation or sulfonylation, according to methods which are described in the literature or which are known to a person skilled in the art.

The compounds of general formulae (I), (II) and (IV) in which $X_1$, $X_2$, $X_3$ and/or $X_4$ represent an $NR_1R_2$, $NR_3COR_4$ or $NR_3SO_2R_5$ group can be obtained from the corresponding compounds of general formulae (I), (II) and (IV) in which $X_1$, $X_2$, $X_3$, and/or $X_4$ represent, for example, a bromine atom by a coupling reaction respectively with an amine, an amide or a sulfonamide in the presence of a base, of a phosphine and of a palladium-based catalyst, according to methods which are described in the literature or which are known to a person skilled in the art.

The compounds of general formulae (I), (II) and (IV) in which $X_1$, $X_2$, $X_3$ and/or $X_4$ represent an $SO_2NR_1R_2$ group can be obtained by a method analogous to that described in *Pharmazie* 1990, 45, 346, or according to methods which are described in the literature or which are known to a person skilled in the art.

The compounds of general formula (I) in which $R_7$ represents a hydrogen atom can be obtained from the compounds of general formula (I) in which, for example, $R_7$ represents a phenylmethyl group by hydrogenation catalyzed by palladium, for example, or by any method which is described in the literature or which is known to a person skilled in the art.

In that which precedes:
- the compounds of general formula (II) are commercially available or are prepared according to numerous processes described in the literature (D. Knittel, *Synthesis*, 1985, 2, 186; T. M. Williams, *J. Med. Chem.*, 1993, 36 (9), 1291; JP2001151771A2, for example);
- the compounds of formula (III) are commercially available or are accessible using methods known to a person skilled in the art;
- the compounds (V) and the other reactants, when their method of preparation is not described, are commercially available or are described in the literature (WO03049702, WO03068749, for example).

The following example describes the preparation of a compound in accordance with the invention. This example is not limiting and only illustrates the present invention. The numbers of the compounds exemplified refer to those given in Table 1. The elementary microanalyses, the LC-MS (liquid chromatography-mass spectrometry) analysis and the IR and/or NMR spectra confirm the structures of the compounds obtained.

Example 1

Compound No. 10

N-(1,2-Dimethyl-1H-benzimidazol-5-yl)-5-fluoro-1-(4,6-dimethylpyridin-2-yl)-1H-indole-2-carboxamide 1.1 Ethyl 5-fluoro-1-(4,6-dimethylpyridin-2-yl)-1H-indole-2-carboxylate 4.35 g (21 mmol) of ethyl 5-fluoro-1H-indole-2-carboxylate, 4.29 g (23.1 mmol) of 2-bromo-4,6-dimethylpyridine, 9.36 g (44.1 mmol) of tripotassium phosphate, 0.66 ml (4.2 mmol) of 1,2-dimethylaminocyclohexane, 0.2 g (1.05 mmol) of copper iodide and 21 ml of dry toluene are added to a pressure tube. The tube is closed and the reaction mixture is stirred at 110° C. for 5 days. After this time, the mixture is poured onto a solution of 100 ml of water and the pH of the medium is adjusted to pH 5 by additions of acetic acid. 100 ml of ethyl acetate are added. The organic phase is separated, washed successively with 50 ml of water and 50 ml of a saturated aqueous sodium chloride solution, then dried over sodium sulfate, filtered and then concentrated under reduced pressure. The residue is purified by preparative chromatography (eluent: dichloromethane/ethyl acetate). 5.56 g of expected product are obtained, which product is used as is in the continuation of the synthesis.

1.2 N-(1,2-Dimethyl-1H-benzimidazol-5-yl)-5-fluoro-1-(4,6-dimethylpyridin-2-yl)-1H-indole-2-carboxamide (Compound No. 10)

1.54 ml of trimethylaluminum (2M in toluene) are added under argon to a solution of 0.34 g (2.11 mmol) of 5-amino-1,2-dimethyl-1H-benzimidazole (WO2002059110) in 19.2 ml of dry toluene. After stirring at 50° C. for 15 minutes, 0.6 g (1.92 mmol) of ethyl 5-fluoro-1-(4,6-dimethylpyridin-2-yl)-1H-indole-2-carboxylate, obtained in Stage 1.1, is added. The reaction mixture is brought to reflux for 4 h and is then stirred at ambient temperature overnight. It is poured onto 150 g of ice and 70 ml of ethyl acetate. The aqueous phase is separated and is extracted with two times 30 ml of ethyl acetate. The organic phases are combined and washed successively with 50 ml of 1 N sodium hydroxide solution, twice with 50 ml of water and then once with 50 ml of a saturated sodium chloride solution. The organic phases are finally dried over sodium sulfate, filtered and then concentrated under reduced pressure. The residue is purified by preparative chromatography (eluent: dichloromethane/methanol). 0.71 g of a solid is obtained, which solid is dried under reduced pressure.

M.p.: 130-140° C.

$^1$H NMR (CDCl$_3$), δ (ppm): 2.4 (s, 3H); 2.57 (s, 3H); 2.58 (s, 3H); 3.71 (s, 3H); 7.15 (m, 7H); 7.6 (m, 2H); 8.7 (s, exchangeable 1H).

The following compounds were prepared by methods similar to that described in Example 1:

N-(1-Methyl-1H-indol-5-yl)-5-fluoro-1-(pyridin-4-yl)-1H-indole-2-carboxamide (Compound No. 1)

$^1$H NMR (CDCl$_3$), δ (ppm): 3.70 (s, 3H); 6.33 (d, 1H); 6.99 (m, 2H); 7.18 (m, 4H); 7.32 (m, 3H); 7.78 (s, 1H); 7.89 (s, 1H); 8.70 (s, 2H).

N-(1-methyl-1H-indol-5-yl)-5-fluoro-1-(pyridin-3-yl)-1H-indole-2-carboxamide (Compound No. 2)

$^1$H NMR (CDCl$_3$), δ (ppm): 3.79 (s, 3H); 6.41 (d, 1H); 7.09 (m, 3H); 7.21 (m, 3H); 7.42 (m, 2H); 7.82 (m, 3H); 8.7 (s, 2H).

N-(1-Methyl-1H-indol-5-yl)-5-fluoro-1-(pyridin-2-yl)-1H-indole-2-carboxamide (Compound No. 3)

$^1$H NMR (DMSO D$_6$), δ (ppm): 3.73 (s, 3H); 6.31 (d, 1H); 7.12 (t×d, 1H); 7.29 (d, 1H); 7.48 (m, 7H); 7.89 (s, 1H); 7.98 (t×d, 1H); 8.52 (m, 1H); 10.41 (s, 1H).

N-(1,2-Dimethyl-1H-benzimidazol-5-yl)-5-fluoro-1-(pyridin-4-yl)-1H-indole-2-carboxamide (Compound No. 4)

$^1$H NMR (d$_6$-DMSO), δ (ppm): 2.50 (s, 3H); 3.72 (s, 3H); 7.19 (t×d, 1H); 7.38 (m, 2H); 7.51 (m, 4H); 7.62 (d, 1H); 7.88 (s, 1H); 8.20 (d, 2H); 10.51 (s, 1H).

N-(1,2-Dimethyl-1H-benzimidazol-5-yl)-5-fluoro-1-(pyridin-2-yl)-1H-indole-2-carboxamide (Compound No. 5)

$^1$H NMR (d$_6$-DMSO), δ (ppm): 2.50 (s, 3H); 3.70 (s, 3H); 7.11 (t×d, 1H); 7.45 (m, 7H); 7.84 (s, 1H); 8.02 (t×d, 1H); 8.55 (d, 1H); 10.49 (s, 1H).

N-(1,2-Dimethyl-1H-benzimidazol-5-yl)-5-fluoro-1-(pyridin-3-yl)-1H-indole-2-carboxamide (Compound No. 6)

$^1$H NMR (CDCl$_3$), δ (ppm): 2.55 (s, 3H); 3.72 (s, 3H); 7.05 (m, 2H); 7.21 (m, 2H); 7.41 (m, 2H); 7.60 (m, 2H); 7.80 (m, 1H); 8.02 (s, 1H); 8.72 (m, 2H).

N-(1-methyl-1H-indol-5-yl)-5-fluoro-1-(4-methylpyridin-2-yl)-1H-indole-2-carboxamide (Compound No. 7)

$^1$H NMR (d$_6$-DMSO), δ (ppm): 2.40 (s, 3H); 3.75 (s, 3H); 6.32 (d, 1H); 7.11 (t×d, 1H); 7.34 (m, 7H); 7.53 (d×d, 1H); 7.91 (s, 1H); 8.39 (d, 1H); 10.38 (s, 1H).

N-(1,2-Dimethyl-1H-benzimidazol-5-yl)-5-fluoro-1-(4-methylpyridin-2-yl)-1H-indole-2-carboxamide (Compound No. 8)

$^1$H NMR (d$_6$-DMSO), δ (ppm): 2.40 (s, 3H); 2.49 (s, 3H); 3.68 (s, 3H); 7.10 (t×d, 1H); 7.24 (d, 1H); 7.40 (m, 6H); 7.82 (s, 1H); 8.38 (d, 1H); 10.45 (s, 1H).

N-(1-Methyl-1H-indol-5-yl)-5-fluoro-1-(2-methylpyridin-4-yl)-1H-indole-2-carboxamide (Compound No. 9)

$^1$H NMR (d$_6$-DMSO), δ (ppm): 2.55 (s, 3H); 3.72 (s, 3H); 6.34 (d, 1H); 7.20 (m, 8H); 7.59 (d×d, 1H); 7.89 (s, 1H); 8.56 (d, 1H); 10.34 (s, 1H).

N-(1-Methyl-1H-indol-5-yl)-5-fluoro-1-(4,6-dimethylpyridin-2-yl)-1H-indole-2-carboxamide (Compound No. 11)

$^1$H NMR (CDCl$_3$), δ (ppm): 2.41 (s, 3H); 2.58 (s, 3H); 3.78 (s, 3H); 6.41 (d, 1H); 7.05 (m, 4H); 7.3 (m, 5H); 7.86 (s, 1H); 8.58 (s, 1H).

The chemical structures and the physical properties of some compounds of general formula (I) according to the invention are illustrated in the following Table 1. In this table, the "M.p." column gives the melting points of the products in degrees Celsius (° C.).

TABLE 1

(I)

| No. | Y | W | M.p. (° C.) |
|-----|---|---|-------------|
| 1 | pyridin-4-yl | 1-methylindol-5-yl | 189-194 |
| 2 | pyridin-3-yl | 1-methylindol-5-yl | 203-205 |
| 3 | pyridin-2-yl | 1-methylindol-5-yl | 210-211 |
| 4 | pyridin-4-yl | 1,2-dimethylbenzimidazol-5-yl | 226-229 |
| 5 | pyridin-2-yl | 1,2-dimethylbenzimidazol-5-yl | 260-261 |
| 6 | pyridin-3-yl | 1,2-dimethylbenzimidazol-5-yl | 139-141 |
| 7 | 4-methylpyridin-2-yl | 1-methylindol-5-yl | 276-279 |
| 8 | 4-methylpyridin-2-yl | 1,2-dimethylbenzimidazol-5-yl | 270-278 |
| 9 | 2-methylpyridin-4-yl | 1-methylindol-5-yl | 213-216 |
| 10 | 4,6-dimethylpyridin-2-yl | 1,2-dimethylbenzimidazol-5-yl | 130-140 |
| 11 | 4,6-dimethylpyridin-2-yl | 1-methylindol-5-yl | 198-199 |

The compounds of the invention have been subjected to in vitro pharmacological trials which have demonstrated their advantage as substances possessing therapeutic activities.

Test of the Inhibition of the Current Induced by Capsaicin with Regard to Rat DRGs Primary Culture of Rat Dorsal Root Ganglion (DRG) Cells:

The neurons of the DRG naturally express the TRPV1 receptor.

Primary cultures of DRGs of newborn rats are prepared from 1-day-old rats. Briefly, after dissection, the ganglions are trypsinized and their cells dissociated mechanically by gentle trituration. The cells are resuspended in an Eagle's basal culture medium comprising 10% of fetal calf serum, 25 mM KCl, 2 mM glutamine, 100 μg/ml of gentamicin and 50 ng/ml of NGF and then deposited on glass cover slips covered with laminin (0.25×10$^6$ cells per cover slip) which are subsequently placed in 12-well Corning dishes. The cells are incubated at 37° C. in a humidified atmosphere comprising 5% of $CO_2$ and 95% of air. Cytosine β-D-arabinoside (1 μM) is added 48 h after culturing, in order to prevent the growth of non-neuronal cells. After culturing for 7-10 days, the cover slips are transferred into experimental chambers for the patch clamp studies.

Electrophysiology:

The measurement chambers (volume 800 μl) comprising the cell preparation are placed on the stage of an inverted microscope (Olympus IMT2) equipped with Hoffman optics (Modulation Contrast, New York) and are observed at a magnification of 400×. The chambers are continuously perfused by gravity (2.5 ml/min) using a distributor of solutions which has 8 inlets, the single outlet of which, composed of a polyethylene tube (opening 500 μm), is placed at least 3 mm from the cell studied. The "whole cell" configuration of the patch clamp technique was used. Borosilicate glass pipettes (resistance 5-10 Mohms) are brought close to the cell using a 3D piezoelectric micromanipulator (Burleigh, PC1000). The overall currents (membrane potential set at −60 mV) are recorded with an Axopatch 1D amplifier (Axon Instruments, Foster City, Calif.) connected to a PC controlled by Pclamp8 software (Axon Instruments). The current plots are recorded on paper and simultaneously recorded digitally (sampling frequency 15 to 25 Hz) and acquired on the hard disk of the PC.

The application of a micromolar capsaicin solution produces an incoming cationic current with regard to the DRG cells (voltage set at −70 mV). In order to minimize the desensitization of the receptors, a minimum interval of one minute between two applications of capsaicin is observed. After a control period (stabilization of the capsaicin alone response), the test compounds are applied alone at a given concentration (concentration of 10 nM or of 0.1 nM) for a period of time of 4 to 5 minutes, during which several capsaicin+compound tests are carried out (obtaining the maximum inhibition). The results are expressed as % of inhibition of the control capsaicin response.

The percentages of inhibition of the capsaicin (1 μM) response are between 20% and 100% for the most active compounds of the invention tested at a concentration from 10 nM to 0.1 nM (see the example in Table 2).

The compounds of the invention are thus effective in vitro antagonists of receptors of TRPV1 type.

TABLE 2

| Compound No. | % Inhibition by the DRG patch technique |
|---|---|
| 10 | 70% (10 nM) |

The results of these trials show that the most active compounds of the invention block the stimulation of the TRPV1 receptors.

The compounds of the invention can thus be used for the preparation of medicaments, in particular for the preparation of a medicament intended to prevent or to treat pathologies in which receptors of TRPV1 type are involved.

Thus, according to another of its aspects, a subject-matter of the invention is medicaments which comprise a compound of formula (I) or a pharmaceutically acceptable salt or also a hydrate or a solvate of the said compound.

These medicaments are employed in therapeutics, in particular in the prevention and/or the treatment of pain and inflammation, chronic, neuropathic (traumatic, diabetic, metabolic, infectious, toxic, induced by an anticancer treatment or iatrogenic), (osteo)arthritic or rheumatic pain, fibromyalgia, back pain, cancer-related pain, trigeminal neuralgia, cephalgia, migraine, dental pain, burns, sunburn, bites or stings, post-herpetic neuralgia, muscle pain, nerve compression (central and/or peripheral), marrow and/or brain trauma, ischaemia (of the marrow and/or brain), neurodegeneration, hemorrhagic vascular accidents (of the marrow and/or brain) or post-stroke pain.

The compounds of the invention can also be used to prevent and/or treat metabolic disorders, such as diabetes.

The compounds of the invention can be used for the preparation of a medicament intended to prevent and/or to treat urological disorders, such as bladder hyperactivity, bladder hyperreflexia, bladder instability, incontinence, urgent urination, urinary incontinence, cystitis, renal colic, pelvic hypersensitivity and pelvic pain.

The compounds of the invention can be used for the preparation of a medicament intended to prevent and/or to treat gynecological disorders, such as vulvodynia, salpingitis-related pain or dysmenorrhea.

These products can also be used for the preparation of a medicament intended to prevent and/or to treat gastrointestinal disorders, such as gastro-oesophageal reflux disorder, stomach ulcers, duodenal ulcers, functional dyspepsia, colitis, IBS, Crohn's disease, pancreatitis, oesophagitis or biliary colic.

Likewise, the products of the present invention may be of use in the prevention and/or the treatment of respiratory disorders, such as asthma, coughs, COPD (chronic obstructive pulmonary disease), bronchoconstriction and inflammatory disorders. These products can also be used to prevent and/or to treat psoriasis, pruritus, irritation of the skin, eyes or mucous membranes, herpes or shingles.

The compounds of the invention can also be used to treat depression.

The compounds of the invention can also be used to treat diseases of the central nervous system, such as multiple sclerosis.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of the said compound, and at least one pharmaceutically acceptable excipient.

The said excipients are chosen, according to the pharmaceutical form and the method of administration desired, from the usual excipients known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the prophylaxis or the treatment of the disorders or diseases mentioned above.

The appropriate unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. The compounds according to the invention can be used, for topical application, in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise doses in order to make possible daily administration of 0.001 to 30 mg of active principle per kg of body weight, depending on the pharmaceutical dosage form.

There may be specific cases where higher or lower dosages are appropriate; such dosages do not depart from the scope of the invention. According to the usual practice, the dosage appropriate to each patient is determined by the physician according to the method of administration and the weight and response of the said patient.

The present invention, according to another of its aspects, also relates to a method for the treatment of the pathologies indicated above which comprises the administration, to a patient, of an effective dose of a compound according to the invention, or one of its pharmaceutically acceptable salts or hydrates or solvates.

What is claimed is:

1. A compound of the formula (I):

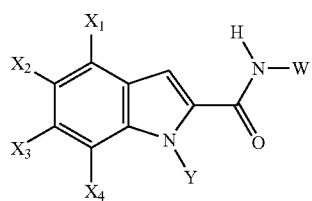

in which:

$X_1$, $X_2$, $X_3$, $X_4$ represent, independently of one another, hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$ or aryl group, the aryl optionally being substituted by one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

W represents a fused bicyclic group of formula:

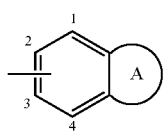

bonded to the nitrogen atom via the 1, 2, 3 or 4 positions;

A represents a 5- to 7-membered heterocycle comprising from one to three heteroatoms chosen from O, S or N; the carbon atom or atoms of A optionally being substituted by one or more groups chosen from a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_3$-alkyleneoxy, aryl, aryl-$C_1$-$C_6$-alkylene, oxo or thio group;

the nitrogen atom or atoms of A optionally being substituted by $R_6$ when the nitrogen is adjacent to a carbon atom substituted by an oxo group, or by $R_7$ in the other cases;

Y represents a heteroaryl optionally substituted by one or more groups chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxyl, $C_1$-$C_6$-fluoroalkoxyl, $C_1$-$C_6$-thiofluoroalkyl, cyano, C(O)$NR_1R_2$, nitro, $NR_1R_2$, $C_1$-$C_6$-thioalkyl, SH, —S(O)—$C_1$-$C_6$-alkyl, —S(O)$_2$—$C_1$-$C_6$-alkyl, —S(O)—$C_3$-$C_7$-cycloalkyl, —S(O)$_2$—, $C_3$-$C_7$-cycloalkyl, $SO_2NR_1R_2$, $NR_3COR_4$, $NR_3SO_2R_5$, aryl-$C_1$-$C_6$-alkylene or aryl group, the aryl and aryl-$C_1$-$C_6$-alkylene optionally being substituted by one or more substitutes chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, halogen, $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ form, together with the nitrogen atom which carries them, an azetidinyl, pyrrolidinyl, piperidinyl, azepinyl, morpholinyl, thiomorpholinyl, piperazinyl or homopiperazinyl group, this group optionally being substituted by a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of one another, hydrogen, $C_1$-$C_6$-alkyl, aryl-$C_1$-$C_6$-alkylene or aryl group;

$R_5$ represents a $C_1$-$C_6$-alkyl, aryl-$C_1$-$C_6$-alkylene or aryl group;

$R_6$ represents hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$—, aryl-$C_1$-$C_6$-alkylene-S(O)$_2$— or aryl group; and wherein it being possible for the sulfur atom or atoms of the heterocycle A or the heteroaryl Y to be in the oxidized form;

it being possible for the nitrogen atom or atoms of the heterocycle A or of the heteroaryl Y to be in the oxidized form;

or a salt thereof.

2. The compound of formula (I) according to claim 1, wherein $X_1$, $X_2$, $X_3$ and $X_4$ represent, independently of one another, hydrogen, halogen, $C_1$-$C_6$-alkyl or $C_1$-$C_6$-fluoroalkyl group; or a salt thereof.

3. The compound of formula (I) according to claim 1, wherein $X_1$, $X_3$ and $X_4$ represent hydrogen; or a salt thereof.

4. The compound of formula (I) according to claim 1, wherein $X_1$, $X_3$ and $X_4$ represent hydrogen and $X_2$ represents halogen; or a salt thereof.

5. The compound of formula (I) according to claim 1, wherein
W represents a fused bicyclic group of formula:

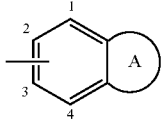

bonded to the nitrogen atom via the 1, 2, 3 or 4 positions; and W is chosen from the indolyl, isoindolyl, indolinyl, isoindolinyl, benzofuranyl, dihydrobenzofuranyl, benzothiophenyl, dihydrobenzothiophenyl, benzoxazolyl, dihydrobenzoxazolinyl, isobenzofuranyl, dihydroisobenzofuranyl, benzimidazolyl, dihydrobenzimidazolyl, indazolyl, benzothiazolyl, isobenzothiazolyl, dihydroisobenzothiazolyl, benzotriazolyl, quinolinyl, dihydroquinolinyl, tetrahydroquinolinyl, isoquinolinyl, dihydroisoquinolinyl, tetrahydroisoquinolinyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[1,4-b]diazepinyl, tetrahydrobenzo[1,4-e]diazepinyl, tetrahydrobenzo[1,4-b]oxazepinyl, tetrahydrobenzo[1,4-b]thiazepinyl groups; the carbon and/or nitrogen atom or atoms of the said group W optionally being substituted as defined in the general formula (I) according to claim 1; or a salt thereof.

6. The compound of formula (I) according to claim 5, wherein W is chosen from the benzimidazolyl and indolyl groups; the carbon atom or atoms of A optionally being substituted by one or more $C_1$-$C_6$-alkyl groups; the nitrogen atom or atoms of A optionally being substituted by $R_7$, $R_7$ representing a $C_1$-$C_6$-alkyl group; or a salt thereof.

7. The compound of formula (I) according to claim 6, wherein W is chosen from the benzimidazol-5-yl and indol-5-yl groups; the carbon atom or atoms of A optionally being substituted by one or more $C_1$-$C_6$-alkyl groups; the nitrogen atom or atoms of A optionally being substituted by $R_7$, $R_7$ representing a $C_1$-$C_6$-alkyl group; or a salt thereof.

8. The compound of formula (I) according to claim 1, wherein Y represents a pyridinyl optionally substituted by one or more $C_1$-$C_6$-alkyl groups; or a salt thereof.

9. A process for the preparation of a compound of formula (I) according to claim 1 comprising:
reacting a compound of formula (IV):

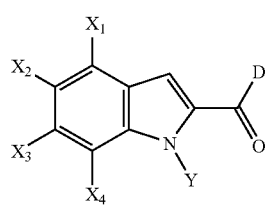

in which $X_1$, $X_2$, $X_3$, $X_4$ and Y are as defined in claim 1 and D represents a $C_1$-$C_6$-alkoxyl group, with an amide of the compound of formula (V):

in which W is as defined in claim 1,
at reflux of a solvent, wherein the amide of the compound of formula (V) being prepared by prior action with trimethylaluminum.

10. A pharmaceutical composition comprising a compound of formula (I) according to claim 1 or a pharmaceutically acceptable salt thereof and at least one pharmaceutically acceptable excipient.

11. A pharmaceutical composition comprising a compound of formula (I) according to claim 2 or a pharmaceutically acceptable salt thereof and at least one pharmaceutically acceptable excipient.

12. A pharmaceutical composition comprising a compound of formula (I) according to claim 3 or a pharmaceutically acceptable salt thereof and at least one pharmaceutically acceptable excipient.

13. A pharmaceutical composition comprising a compound of formula (I) according to claim 4 or a pharmaceutically acceptable salt thereof and at least one pharmaceutically acceptable excipient.

14. A pharmaceutical composition comprising a compound of formula (I) according to claim 5 or a pharmaceutically acceptable salt thereof and at least one pharmaceutically acceptable excipient.

15. A pharmaceutical composition comprising a compound of formula (I) according to claim 6 or a pharmaceutically acceptable salt thereof and at least one pharmaceutically acceptable excipient.

16. A pharmaceutical composition comprising a compound of formula (I) according to claim 7 or a pharmaceutically acceptable salt thereof and at least one pharmaceutically acceptable excipient.

17. A pharmaceutical composition comprising a compound of formula (I) according to claim 8 or a pharmaceutically acceptable salt thereof and at least one pharmaceutically acceptable excipient.

18. A method of treating a disease selected from the group consisting of pain and irritation of the skin, eyes and mucous membrane, comprising administering to a patient in need of said treatment a therapeutically effective amount of a compound of formula (I) according to claim 1.

19. A method of treating a disease in a patient, which disease is selected from the group consisting of inflammation, urological disorders, gynecological disorders, respiratory disorders, multiple sclerosis and depression, comprising administering to said patient a therapeutically effective amount of a compound of formula (I) according to claim 1.

20. A method of treating a disease in a patient, which disease is selected from the group consisting of metabolic disorders, gastrointestinal disorders, psoriasis, pruritis, herpes and shingles, comprising administering to said patient a therapeutically effective amount of a compound of formula (I) according to claim 1.

* * * * *